United States Patent
Reynolds et al.

(10) Patent No.: US 11,808,756 B2
(45) Date of Patent: Nov. 7, 2023

(54) SENSOR CLIP FOR STACKED SENSOR DISPENSING SYSTEM, AND SYSTEMS, METHODS AND DEVICES FOR MAKING AND USING THE SAME

(71) Applicant: Ascensia Diabetes Care Holdings AG, Basel (CH)

(72) Inventors: Jeffery S. Reynolds, New Fairfield, CT (US); Eugene R. Prais, West Milford, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 372 days.

(21) Appl. No.: 16/896,498

(22) Filed: Jun. 9, 2020

(65) Prior Publication Data
US 2020/0300837 A1    Sep. 24, 2020

Related U.S. Application Data

(63) Continuation of application No. 15/318,433, filed as application No. PCT/US2015/035654 on Jun. 12, 2015, now Pat. No. 10,712,335.
(Continued)

(51) Int. Cl.
*G01N 33/487* (2006.01)
*A61B 5/15* (2006.01)
(Continued)

(52) U.S. Cl.
CPC ....... *G01N 33/48757* (2013.01); *A61B 5/157* (2013.01); *A61B 5/150022* (2013.01);
(Continued)

(58) Field of Classification Search
CPC ......... G01N 33/48757; G01N 27/3272; G01N 27/3273; G01N 33/48778; G01N 21/78;
(Continued)

(56) References Cited

U.S. PATENT DOCUMENTS 5,120,420 A   6/1992   Nankai
5,194,393 A   3/1993   Hugl
(Continued)

FOREIGN PATENT DOCUMENTS

JP    H07-311201 A    11/1995
JP    H08-043405 A    2/1996
(Continued)

OTHER PUBLICATIONS

International Search Report, PCT/US2015/034654, dated Aug. 28, 2015 (3 pages).
(Continued)

*Primary Examiner* — Matthew D Krcha
*Assistant Examiner* — Sophia Y Lyle
(74) *Attorney, Agent, or Firm* — ERISE IP, P.A.

(57) ABSTRACT

Sensor clip assemblies, sensor clips, analyte testing systems, and methods for making and using the same are disclosed. A sensor clip assembly is disclosed for storing and dispensing analyte testing sensors. The sensor clip assembly includes numerous test sensors arranged in a stack. Each test sensor is configured to assist in testing an analyte in a fluid sample. The sensor clip assembly also includes a skeletal frame with a top, a bottom, and numerous sides. The top, bottom and sides are interconnected to define an internal chamber within which is stored the stack of test sensors. At least one of the sides includes one or more elongated rails with structural gaps on opposing sides thereof. For some configurations, multiple sides of the skeletal frame comprise at least one or multiple elongated rails, each of which has structural gaps on opposing sides thereof and may be columnar in nature.

20 Claims, 6 Drawing Sheets

Related U.S. Application Data

(60) Provisional application No. 62/014,429, filed on Jun. 19, 2014.

(51) Int. Cl.
*A61B 5/157* (2006.01)
*B65D 83/08* (2006.01)
*C12Q 1/00* (2006.01)
*G01N 27/327* (2006.01)
*G01N 21/78* (2006.01)
*G01N 21/77* (2006.01)

(52) U.S. Cl.
CPC .. *A61B 5/150305* (2013.01); *A61B 5/150358* (2013.01); *B65D 83/0823* (2013.01); *C12Q 1/006* (2013.01); *G01N 27/3272* (2013.01); *G01N 27/3273* (2013.01); *G01N 33/48778* (2013.01); *G01N 21/78* (2013.01); *G01N 2021/7759* (2013.01)

(58) Field of Classification Search
CPC ....... G01N 2021/7759; G01N 33/4875; G01N 33/66; A61B 5/150022; A61B 5/150305; A61B 5/150358; A61B 5/157; A61B 2562/0295; A61B 5/14532; A61B 5/1486; A61B 2562/085; A61B 5/14546; A61B 5/1495; B65D 83/0823; C12Q 1/006
See application file for complete search history.

(56) References Cited

U.S. PATENT DOCUMENTS

| | | | |
|---|---|---|---|
| 5,575,403 A | 11/1996 | Charlton | |
| 5,630,986 A | 5/1997 | Charlton | |
| 5,660,791 A | 8/1997 | Brenneman | |
| 5,759,364 A | 6/1998 | Charlton | |
| 5,798,031 A | 8/1998 | Charlton | |
| 5,810,199 A | 9/1998 | Charlton | |
| 5,856,195 A | 1/1999 | Charlton | |
| 7,138,089 B2 | 11/2006 | Aitken | |
| 7,677,409 B2 | 3/2010 | Reynolds | |
| 7,809,512 B2 | 10/2010 | Perry | |
| 7,875,243 B2 | 1/2011 | Rush | |
| 8,097,210 B2 | 1/2012 | Ruan | |
| 8,124,014 B2 | 2/2012 | Charlton | |
| 8,153,080 B2 | 4/2012 | Kheiri | |
| 8,202,488 B2 | 6/2012 | Jung | |
| 8,206,564 B2 | 6/2012 | Schell | |
| 8,574,510 B2 | 11/2013 | Gofman | |
| 10,712,335 B2 | 7/2020 | Reynolds | |
| 2002/0037238 A1* | 3/2002 | Haar | G01N 27/3273 422/68.1 |
| 2003/0116583 A1* | 6/2003 | Pugh | G01N 33/48757 221/268 |
| 2004/0178216 A1* | 9/2004 | Brickwood | G01N 33/48757 221/268 |
| 2004/0208785 A1* | 10/2004 | Seto | G01N 33/48757 422/63 |
| 2006/0182656 A1* | 8/2006 | Funke | G01N 33/48757 422/400 |
| 2008/0094804 A1* | 4/2008 | Reynolds | A61B 5/150305 361/727 |
| 2008/0131322 A1 | 6/2008 | Kheiri | |
| 2009/0114673 A1* | 5/2009 | Matsumoto | G01N 33/48757 221/268 |
| 2009/0301166 A1* | 12/2009 | Charlton | G01N 33/48757 73/1.02 |
| 2011/0040165 A1* | 2/2011 | Williams, III | A61B 5/150358 206/305 |
| 2012/0082597 A1 | 4/2012 | Doniger | |
| 2013/0324822 A1 | 12/2013 | Prais | |

FOREIGN PATENT DOCUMENTS

| | | |
|---|---|---|
| JP | 2004-239893 A | 8/2004 |
| JP | 2005-522243 A | 7/2005 |
| JP | 2008-504532 A | 2/2008 |
| JP | 2008-527383 A | 7/2008 |
| JP | 2014-081389 A | 5/2014 |
| WO | WO 02/08753 A2 | 1/2002 |
| WO | WO 2003/073090 A1 | 2/2003 |
| WO | WO 2012/138451 A2 | 10/2012 |
| WO | WO 2012/160242 A1 | 11/2012 |
| WO | WO 2013/187031 A1 | 6/2013 |
| WO | WO 2013/180804 A1 | 12/2013 |

OTHER PUBLICATIONS

Written Opinion of the International Searching Authority, PCT/US2015/034654, dated Aug. 28, 2015 (6 pages).

English Translation of Office Action from Patent Application No. JP-2016-573934 dated Mar. 19, 2019.

Extended European Search Report for Application No. EP 20153966.5, dated Feb. 17, 2020 (7 pages).

\* cited by examiner

--Prior Art--
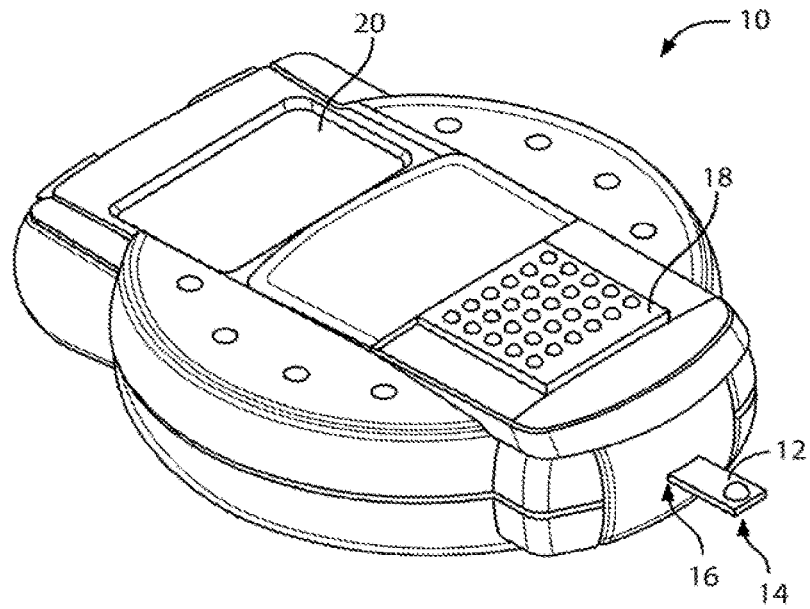
FIG. 1
FIG. 2
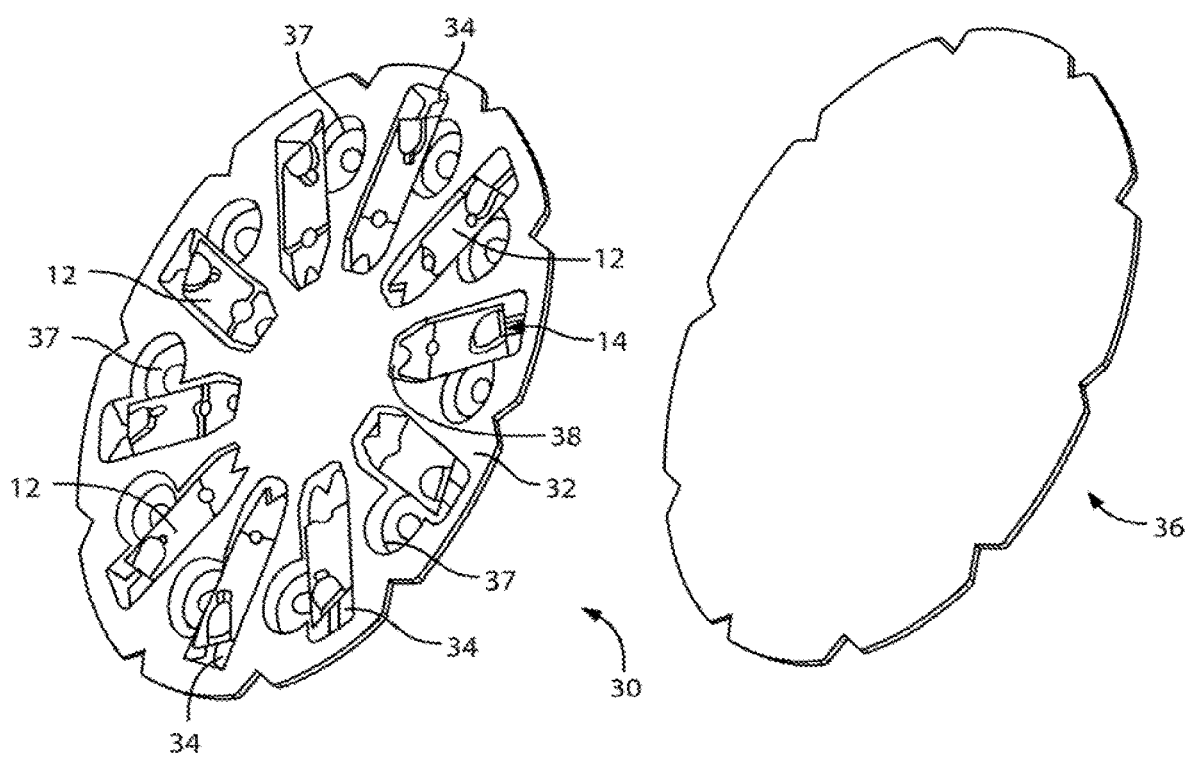
--Prior Art--

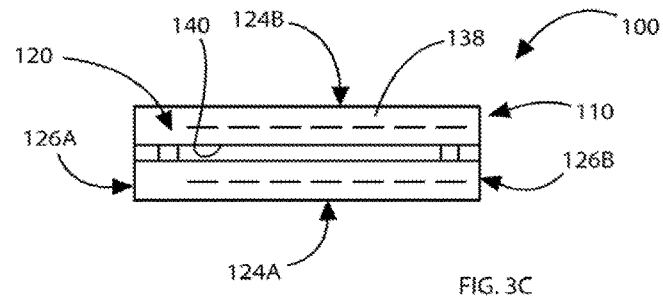
FIG. 3C
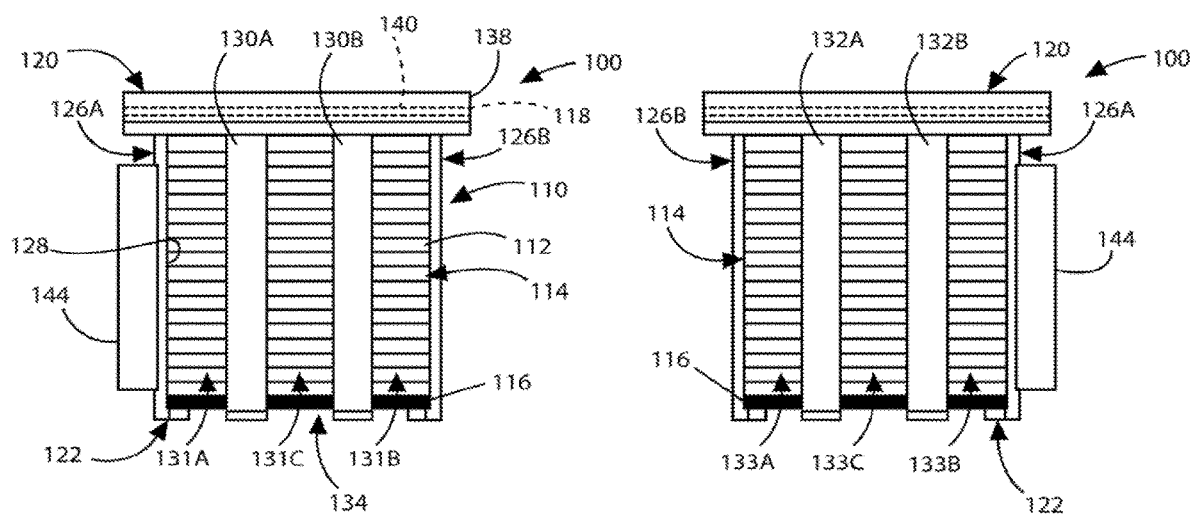
FIG. 3A
FIG. 3B
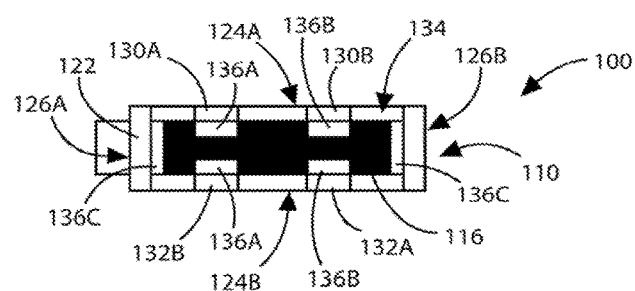
FIG. 3D

SENSOR CLIP FOR STACKED SENSOR DISPENSING SYSTEM, AND SYSTEMS, METHODS AND DEVICES FOR MAKING AND USING THE SAME

CROSS REFERENCE TO RELATED APPLICATIONS

The application is a continuation of U.S. Application Ser. No. 15/318,433, filed Dec. 13, 2016, now allowed, which is a U.S. national stage entry of International Application Serial No. PCT/US2015/035654, filed Jun. 12, 2015, claims priority to U.S. Provisional Patent Application Ser. No. 62/014,429, filed on Jun. 19, 2014, the contents of each of which are hereby incorporated by reference herein in their entireties.

TECHNICAL FIELD

The present disclosure relates generally to systems, methods, and devices for determining an analyte concentration in a fluid sample. More particularly, aspects of the present disclosure relate to containers for storing and dispensing sensors for testing analytes.

BACKGROUND

The detection of a wide range of analytes present in fluid samples is of great importance in the diagnoses and maintenance of certain physiological abnormalities. Quantitative analysis of analytes in bodily fluids, for example, is necessary for the detection, management, and treatment of many degenerative medical conditions. For example, lactate, cholesterol, and bilirubin should be monitored in certain individuals. In addition, determining glucose in body fluids is important to diabetic individuals who must frequently check their blood glucose levels to regulate the carbohydrate intake in their diets. Failure to monitor glucose levels and take corrective action can have serious implications fora diabetic individual. When blood glucose levels drop too low—a condition known as hypoglycemia—a person can become nervous, shaky, and confused, and may become physically impaired and eventually pass out. A person can also become very ill if their blood glucose level becomes too high—a condition known as hyperglycemia—which, like hypoglycemia, is a potentially life-threatening condition.

Many conventional hand-held glucose testing devices ("meters") utilize test strips that provide an indication of the presence and/or concentration of a particular substance within the body fluid being analyzed. These test strips are often thin strips of material, such as paper or plastic, which are coated or impregnated with a chemical reagent, A reagent is a substance or compound that is used to detect, measure, examine, or produce other substances by chemically reacting with a given substance present: in a test sample. When the test strip comes into contact with a body fluid, such as blood or interstitial fluid, the test strip "harvests" the body fluid, e.g., fluid is drawn into a capillary channel that transfers the fluid by capillary action to the reagent material. If a given substance is present in the body fluid, the reagent chemically reacts with that substance. The reaction of the reagent, upon contact with the body fluid, can be analyzed (e.g., electrochemically or optically) to determine the presence anal/or concentration of a particular substance.

Many test strip reagents are sensitive to the effects of ambient humidity and sunlight. One way to reduce or eliminate the effects of humidity and sunlight is to individually package each of the sensors with desiccant. Individually packaging each strip, however, increases manufacturing time and costs, and inflates packaging and shipping costs, all of which result in increased costs to the end user. To reduce costs and improve ergonomics, containers have been designed to store and dispense multiple test sensors, thereby eliminating the need to individually package each test strip. Examples of some containers for storing a stack of test sensors can be found in U.S. Pat. Nos. 7,677,409, 7,875,243, 8,097,210 and 8,153,080 and U.S. Patent Appl. Pub, No, US2013/0324822 A1, each of which is incorporated herein by reference in its entirety. Many of these containers enclose the sensor stack in a hermetically sealed, rigid outer housing. Some of the containers are provided with a mechanical dispensing mechanism to feed the test sensors, one at a time, for testing by the user. This configuration provides ease of use to normal users and is especially important for those users who may have some physical limitations.

Shown respectively in FIGS. 1 and 2 are examples of a hand-held analyte testing device 10 ("meter") and a package 30 of test strips 12 ("test strip pack"). The test strip pack 30 of FIG. 2 is designed to be housed within the analyte testing device 10 of FIG. 1. The testing device 10 has a display device 20 for displaying information (e.g., analyte concentration readings) to the user. The analyte testing device 10 also includes a slider 18, which cooperates with an "ejection" mechanism inside the testing device 10 for advancing test strips 12 from the package 30 for harvesting a sample of fluid. Prior to each test, an individual test strip 12 is pushed by the ejection mechanism through the package 30 such that a collection area 14 of the test strip 12 is extended from the testing device 10 through a slot 16 formed in the housing of the meter 10. As seen in FIG. 1, the collection area 14 projects from the testing device 10, while a contact area of the test strip 12 (visible in FIG. 2), which is disposed at the opposite end of the strip 12, remains inside of the testing device 10, in electrochemical configurations, the contact area includes terminals that electrically couple test strip electrodes to testing instrumentation disposed within the testing device 10. This instrumentation is configured to measure the oxidation current produced at the electrodes by the reaction of glucose and the reagent.

A circular array of test strips 12 is shown in FIG. 2 disposed inside of the test strip pack 30. The test strip pack 30 comprises a disk-like circular container 32 with ten individual compartments 34—referred to in the art as "blisters"—arranged radially on the circular container 32. The circular container 32 is made from an aluminum foil/plastic laminate which is sealed with a burst foil cover 36 to isolate the sensors 12 from ambient humidity, sunlight, and from adjacent sensors. Each test strip 12 is kept dry by a desiccant located inside a desiccant compartment 37 disposed adjacent to the compartment 34. Further details of the manufacture, configuration, and operation of the testing device 10 and test strip pack 30 are provided, for example, in U.S. Pat. Nos. 5,630,986, 5,575,403, 5,810,199 and 5,856,195.

A drawback associated with the circular array of test strips 12 of FIG. 2 is the large area that is required to house the test strip pack 30. Size restrictions for band-held testing devices that internally house flat test strip packs constrain the size of the package, which restricts the number of test strips that can be provided in each package. Having a low number of strips in the disk results in a higher per strip cost for the package which is not desirable since in vitro diagnostic assays and, especially, glucose monitoring test strips are faced with continuing downward pressure on selling prices. Similarly, a drawback associated with conventional flip-top containers and screw-tight sensor bottles is the overall complexity of each container and the amount of material required to fabricate each container, in addition, the manual operations required for closing and opening test sensor bottles and for removing strips from the bottle is oftentimes not convenient, which discourages patient testing even though increased patient testing is associated with better glucose management. Customer convenience is another key factor in influencing compliance to a regular testing regimen. In addition, it is often necessary for a person with diabetes to test while "on the go" where manual manipulation of a bottle and strips can be very difficult. Finally, the large cylindrical foot print of a bottle necessitated by the need to retrieve strips by finger is not conducive to portability. What is needed then is a test sensor container configuration that can store a larger quantity of sensors in a small area, while maintaining customer convenience and offering low-cost manufacturing options for the sensor and packaging.

SUMMARY

Disclosed herein are low-cost test-sensor clips with intuitive and convenient strip handling. These test-sensor clip systems can provide a unique, low-cost means to offer 25-strip, 50-strip, 100-strip, or N-strip cartridge convenience in a low-cost disposable or reusable package. Because the test strips are held in a small, low-cost clip that can be injection molded, there is very little cost in the strip package. In addition, the sensor stack and clip can readily be foil wrapped in a reagent-grade foil package with a desiccant material. Because the clip and meter can automate sensor handling, the individual strips can be made smaller than their conventional counterparts. This, in turn, can significantly reduce the strip cost by reducing raw materials and increasing the throughput of manufacturing capital and overhead. For some configurations, the clip can have an auto-calibration label that would allow for better calibration, inclusion of anti-counterfeiting measures, geographic information, date of manufacture information, etc. Limiting the disposable part cost count and strip size offers real customer savings with a lower per-strip cost as compared to sensor bottles, blister packs, or other prior art container configurations. This allows for increased customer convenience while offering a low-cost manufacturing option for the sensors and packaging, an intuitive user experience, and a compact, reliable, and low-cost glucose meter. In addition, smaller sensors and reduced packaging are also more environmentally friendly.

The foregoing features and options of the low-cost test sensor clip could also be applied to a durable flip-top bottle, which is separate from the testing meter. In this configuration, the flip-top bottle would provide cost, environmental, form factor, and convenience advantages while still allowing compatibility with existing meters. The flip-top bottle could be configured with an ejection mechanism to eject the strips, electrodes first, to eliminate strip handling by allowing the user to transfer the test strip directly from the bottle to a meter. This would be especially useful in point of care and/or hospital meters where there is concern about contamination from blood borne pathogens.

Some of the disclosed concepts are directed to a sensor clip assembly for storing and dispensing analyte testing sensors. The sensor clip assembly includes a plurality of test sensors arranged in a stack. Each of the test sensors is configured to assist in testing an analyte in a fluid sample. The sensor clip assembly also includes a skeletal frame with a top, a bottom, and a plurality of sides. The top, bottom and sides of the skeletal frame are interconnected to define an internal chamber within which is stored the stack of test sensors, At least one of the sides includes one or more elongated rails with structural gaps on opposing sides thereof. For some configurations, multiple sides or all of the sides of the skeletal frame comprise or consist essentially of one or more elongated rails, each of which has structural gaps on opposing sides thereof and may be columnar in nature.

Other disclosed concepts are directed to a sensor clip for retaining a stack of test strips. Each of the test strips is configured to assist in testing at least one analyte. The sensor clip includes a top, a bottom, and a plurality of sides that connect the top with the bottom to define therebetween an internal chamber within which is seated the stack of test strips. At least one of the sides comprises or consists essentially of one or more elongated rails with structural gaps on opposing sides thereof. In some embodiments, multiple sides or all of the sides of the sensor clip comprise or consist essentially of one or more elongated rails, each of which has structural gaps on opposing sides thereof and may be columnar in nature.

Aspects of the present disclosure are directed to an analyte testing system. This analyte testing system includes multiple test sensors arranged in a stack. Each test sensor is configured to receive a fluid sample and generate an indication of a characteristic of an analyte in the fluid sample. The analyte testing system also includes a hand-held meter with an outer housing defining an internal cartridge chamber with an opening. The meter may include an optional lid that is movably attached to the outer housing to cover the internal cartridge chamber opening when the lid is in a closed position. The meter also includes testing electronics stowed within the housing and configured to analyze the indication of the characteristic of the analyte generated by each of the test sensors. A sensor clip is removably disposed inside the internal cartridge chamber of the meter. The sensor clip includes a skeletal frame with a top, a bottom, and a plurality of sides. The top, bottom and sides of the skeletal frame are interconnected to define an internal sensor chamber within which is stowed the stack of test sensors. At least one of the sides includes one or more elongated rails with structural gaps on opposing sides thereof. Optionally, two or more or all of the skeletal frame sides comprises or consists essentially of elongated rails, each of which has structural gaps on opposing sides thereof and may be columnar in nature.

For any of the disclosed configurations, the bottom of the skeletal frame of the sensor clip may define an aperture configured to receive therethrough the stack of test sensors. The skeletal frame may further comprise a pair of opposing flexible tabs proximal the aperture. The tabs may be configured to flex such that the stack of test sensors can pass through the aperture in the bottom of the skeletal frame and into the internal chamber. The flexible tabs may be configured to retain the stack of test sensors inside the internal chamber. As another optional feature, one or more of the sides of the skeletal frame may comprise one or more compliant alignment rails configured to align the stack of test sensors within the internal chamber. An optional desiccant pocket can be attached to the skeletal frame, the pocket storing therein a desiccant material. The desiccant material could also be co-molded to the skeletal frame or attached during assembly. The desiccant pocket/material could also double as a functional component of the assembly, for example as a rigid base plate on which the strip stack sits.

The above summary is not intended to represent each embodiment or every aspect of the present disclosure. Rather, this summary merely provides an exemplification of some of the novel features presented herein. The above features and advantages, and other features and advantages of the present disclosure, will be readily apparent from the following detailed description of exemplary embodiments and modes for carrying out the present invention when taken in connection with the accompanying drawings and the appended claims.

BRIEF DESCRIPTION OF THE DRAWINGS

FIG. 1 is a perspective-view illustration of an example of a hand-held analyte testing device.

FIG. 2 is a partially exploded perspective-view illustration of an example of a test strip pack.

FIGS. 3A-D are front, back, top and bottom view illustrations, respectively, of a representative stacked sensor clip assembly for multi-strip analyte testing devices and systems in accordance with aspects of the present disclosure.

FIGS. 4A and 48 are partially broken away side-view illustrations of an example of an analyte testing meter for use with the sensor clip assembly shown in FIGS. 3A-D is accordance with aspects of the present disclosure.

Figure 4B:
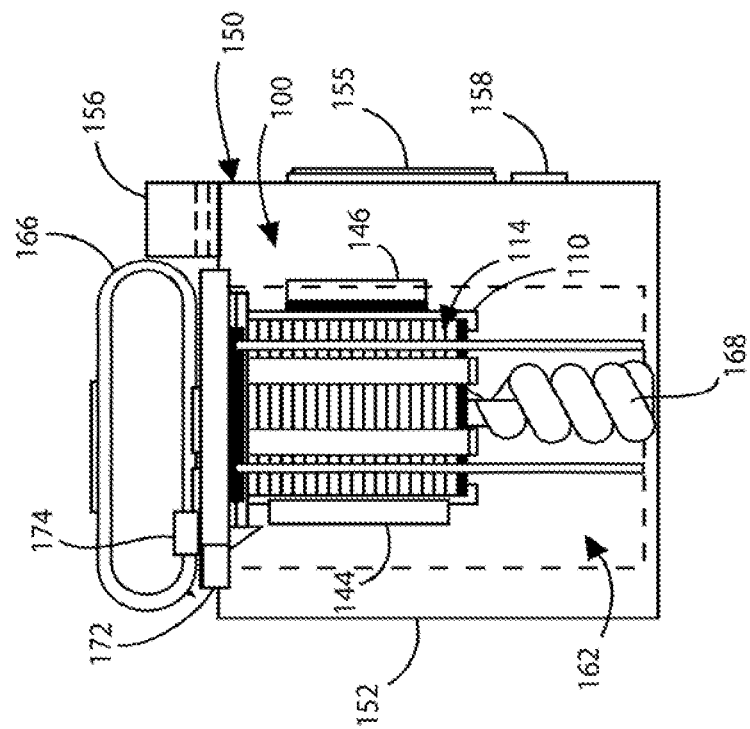

While aspects of this disclosure are susceptible to various modifications and alternative forms, specific embodiments are shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

This invention is susceptible of embodiment in many different forms. There are shown in the drawings and will herein be described in detail representative embodiments of the invention with the understanding that the present disclosure is to be considered as an exemplification of the principles of the invention and is not intended to limit the broad aspects of the invention to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference or otherwise. For purposes of the present detailed description, unless specifically disclaimed: the singular includes the plural and vice versa; the words "and" and "or" shall be both conjunctive and disjunctive; the word "all" means "any and all"; the word "any" means "any and all"; and the words "including" and "comprising" mean "including without limitation." Moreover, words of approximation, such as "about," "almost," "substantially," "approximately," and the like, can be used herein in the sense of "at, near, or nearly at,", or "within 3-5% of," or "within acceptable manufacturing tolerances," or any logical combination thereof, for example.

Aspects of the present disclosure are directed to a simple, low-cost, compact, and light-weight clip that holds a stack of analyte testing strips (e.g., 50+ sensors/stack). In contrast to prior art sensor cartridges that are designed as fully-encapsulating enclosures, such as screw-tight bottles, blister packs, and moisture-proof cartridges, the sensor clip has a skeletal frame with sides comprising one or more elongated, columnar rails for retaining the stack of sensors. The stacked-sensor clip assembly can be packaged inside a reagent-grade foil wrapping with a desiccant material for storage and shipping of the sensor clip assembly. The low-cost, reagent-grade foil package protects the test strips by acting as both a vapor barrier and a guard against sunlight. The foil-wrapped sensor clip assembly can be commercialized as the final consumer product; additionally or alternatively, an external box could be used to provide the requisite protection for the sensors. There is no requirement that the sensor clip assembly be sealed in an additional outer casing that would otherwise increase the amount of material and the overall number of parts. It may also be desirable, for some applications, that the disposable sensor clip be fabricated without an ejection mechanism or a biasing member. After being removed from the foil package and/or box, the sensor clip assembly can be loaded as-is into a meter.

One or more or all of the disclosed configurations can offer no-strip-handling convenience with ultralow-cost sensor packaging, which results from a low disposable part count and a small strip size. Other advantages can include automated, highly intuitive strip handling, as well as strip storage in a small rectangular package that has a lower volume and is a more convenient form factor compared to conventional sensor cartridges. Decreased environmental impact is also achieved through smaller test strips, a low-part-count clip, and a foil package that, singly and collectively, produce a smaller waste stream than conventional disposable sensor cartridges. Additional advantages and options may include (in any combination): a low-cost, simple and reliable strip-excision mechanism made with few moving parts; detailed calibration and other information provided on the clip for improved performance and robust anti-counterfeiting; reduced chance of having strip temperatures that are significantly different than meter temperatures because, once the clip is loaded, strips are exposed to a similar environment; and, a flip-top lid on the meter with a temperature sensor to detect temperature mismatches between the meter and the environment.

Referring now to the drawings, wherein like reference numerals refer to like features throughout the several views, there is shown in FIGS. 3A-3D a representative sensor clip assembly, designated generally as 100, for storing and dispensing analyte testing sensors in accordance with aspects of the present disclosure. For purposes of explanation, the illustrated embodiments are generally described herein with regard to meters and sensors for analyzing the concentration of glucose in a blood sample. However, the aspects of the present invention are not intended to be limited to this specific application. The presently disclosed embodiments may be configured to determine one or more characteristics of other analytes in other types of samples. For example, the meters and test strips may measure lipid profiles (e.g., cholesterol, triglycerides, low-density lipoprotein (LDL), high-density lipoprotein (HDL), etc.), microalbumin, hemoglobin A1c, fructose, lactate, bilirubin, or other analytes. The analytes may be in, for example, a whole blood sample, a blood serum sample, a blood plasma sample, or body fluids, such as interstitial fluid (ISF) and urine, or other (non-body) fluid samples.

Figure 4A:
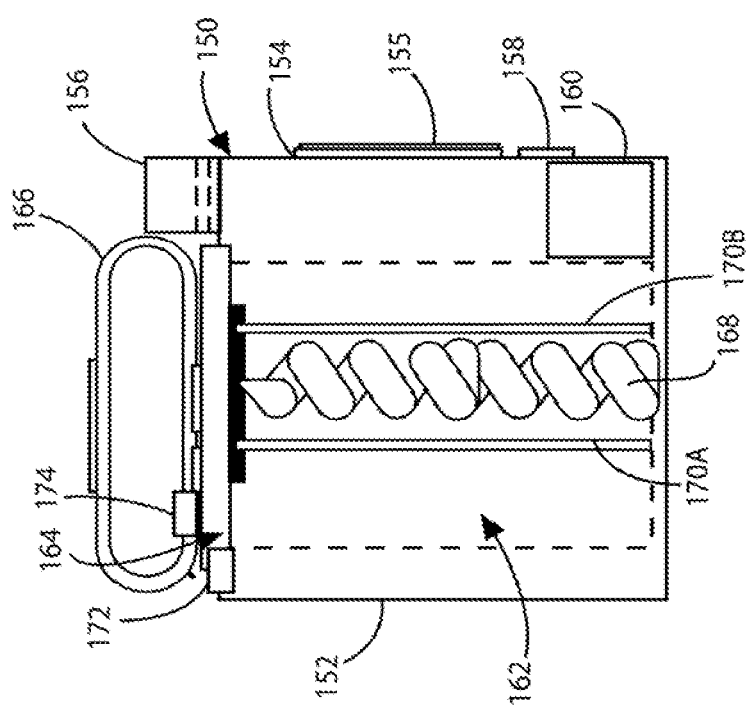

FIG. 3A provides a side-view illustration of a cartridge or "sensor clip" 110 for use in a multi-strip analyte testing meter, such as the hand-held glucose meter 150 shown in FIGS. 4A and 4B. Sensor clip 110 can be used to both store and dispense a plurality of biosensors or test strips (one of which is designated as 112 in FIG. 3A), such as the test strips 12 described above in connection with FIGS. 1 and 2. According to the embodiment illustrated in FIGS. 3A-3D, the test strips 112 (also referred to herein as "test sensors") are laid flat, arranged substantially one on top of the next in a stack 114, and seated on top of an optional push plate 116. Generally, in use, the test strips 112 are dispensed from the top 120 of the sensor clip 110, one at a time, through a sensor slot 118 in a cap 138. While the push plate 116 is illustrated in the figures as a part of the clip assembly 110, alternative configurations are assembled without the push plate 116 (e.g, a push plate or similarly functioning structure is provided by the testing meter). As another option, the push plate 116 can be made of or encapsulate desiccant material.

Each of the test strips 112 is configured to assist in testing an analyte glucose) in a fluid sample (e.g., blood). As explained above with respect to the test strips 12 of FIGS. 1 and 2, each of the test strips 112 of FIGS. 3A-3C is configured to receive a blood sample, and contemporaneously generate an indication of a characteristic of glucose in the blood. The test sensors may take on various forms, including electrochemical biosensors and/or optical biosensors. Electrochemical biosensors include a regent designed to chemically react with glucose in a blood sample to create an oxidation current at electrodes disposed within the electrochemical biosensor. The oxidation current that is generated by the biosensor is directly proportional to the user's blood glucose concentration. Non-limiting examples of electrochemical biosensors are described in U.S. Pat. Nos. 5,120,420, 5,660,791, 5,759364 and 5,798,031. Optical biosensors, in contrast, incorporate a reagent that is designed to produce a colorimetric reaction indicative of a user's blood glucose concentration level. The colorimetric reaction can then be read by a spectrometer incorporated into the testing device. Some non-limiting examples of optical biosensors are described, for example, in U.S. Pat. Nos. 5,194,393 and 8,202,488.

Each of the test strips 112 may contain biosensing or reagent material that reacts with, for example, blood glucose. The test strip 112 can be a multilayer test sensor that includes a base or substrate with a lid. For some multilayer test sensor configurations, the test strip 112 includes a spacer between the base and lid. The test sensor may harvest the fluid sample using a capillary channel. For an electrochemical test sensor configuration, the test strip 112 includes at least two electrodes (e.g., a counter electrode and a working (measuring) electrode) in the form of a metallic electrode pattern. A potential is applied across these electrodes and a current is measured at the working electrode.

The reagent converts the analyte of interest (e.g., glucose) in the fluid sample (e.g., blood) into a chemical species that is measurable. The reagent typically includes an enzyme and a mediator. For example, if the analyte of interest is glucose, the enzyme may be glucose dehydrogenase (GDH) or glucose oxidase. A mediator is an electron acceptor that assists in generating a current that corresponds to the analyte concentration. Non-limiting examples of mediators include ferricyanide (e.g., potassium ferricynaide), phenothizaines (e.g., 3-phenylimino-3H-phenothiazine), phenoxazines 3-phenyliminio-3H-phenoxazine). The reagent may include binders that hold the enzyme and mediator together, other inert ingredients, or combinations thereof. The reagent may include additional ingredients such as a buffer, polymer, surfactant or any combination thereof in some embodiments.

In the illustrated embodiment, the sensor clip 110 includes a top 120, a bottom 122, and a plurality of sides, namely first and second lateral sides 124A and 124B, respectively, and first and second longitudinal sides 126A and 126B, respectively. The top 120, bottom 122, and sides 124A, 124B, 126A, 126E of the sensor clip 110 are interconnected (e.g., injection molded as a single, unitary piece) to define an internal chamber 128 within which is retained and stored the stack 114 of test sensors 112. Although alternative shapes are certainly envisioned as being within the scope of the present disclosure, the sensor clip 110 is portrayed with a polyhedral shape having six generally rectangular outer faces. The sensor clip 110 may optionally include greater or fewer than six faces, each of which may take on a different size and/or shape than that shown in the drawings. In this regard, the drawings presented herein are not to scale and are provided purely for instructional purposes. Thus, the specific and relative dimensions shown in the drawings are not to be considered limiting.

By way of contrast to prior art sensor cartridges that are designed as fully-encapsulating enclosures, the sensor clip 110 of FIGS. 3A-3D comprises a skeletal frame with one or more "open" faces. As a non-limiting example, at least one side of the sensor clip's 110 skeletal frame comprises an elongated rail with structural gaps on opposing sides thereof. As used herein, a "structural gap" includes an opening, break, or space (i.e., an absence of structure) between adjacent solid structures. By way of illustration, and not limitation, the first lateral side 124A of the skeletal frame comprises or consists essentially of two adjacent, substantially parallel, elongated rails 130A and 130B that are spaced from one another by a centrally located structural gap 131C that is disposed between and extends the entire length of the rails 130A, 130B, as seen in FIG. 3A. Each of the elongated rails 130A, 130B is also spaced from one of the longitudinal sides 126A, 126B of the sensor clip's 110 skeletal frame by a respective intermediate structural gap 131A and 131B that extends the entire length of the rails 130A, 130B. Each rail 130A, 130B of FIG. 3A is columnar, extending between and connecting the top 120 and the bottom 122 of the skeletal frame. Alternatively, one or more of the rails 130A, 130B can be transversely oriented, extending between and connecting the longitudinal sides 126A, 126B of the skeletal frame, or can take on other orientations and configurations within the scope and spirit of this disclosure.

Optionally, the second lateral side 124B of the clip's 110 skeletal frame comprises or consists essentially of two adjacent, substantially parallel, elongated rails 132A and 132B that are spaced from one another by a centrally located structural gap 133C that is disposed between and extends the entire length of the rails 132A, 132B, as seen in FIG. 3B. Each of the elongated rails 132A, 132B is also spaced from one of the longitudinal sides 126B, 126A of the sensor clip's 110 skeletal frame by a respective intermediate structural gap 133A and 133B that extends the entire length of the rails 132A, 132B. Each 132A, 132B rail is columnar, extending between and connecting the top 120 and the bottom 122 of the skeletal frame. Like the rails 130A, 130B of FIG. 3A, one or more of the rails 132A, 132B of FIG. 3B can be transversely oriented or can take on other orientations and configurations. To that end, the number of rails on each side may vary from that which is shown in the drawings. It is also envisioned that one or both of the longitudinal sides 126A, 126B have open faces, e.g., comprising or consisting essentially of one or more elongated rails.

Referring to FIG. 3D, the bottom of the sensor clip's 110 skeletal frame defines an aperture 134 which is shaped and sized to receive therethrough the stack 114 of test sensors 112. The base 122 of the sensor clip 110 may be provided with retention means to secure or otherwise retain the test sensor stack 114 inside the internal chamber 128. The retention means may take on various thrifts, such as a base plate, spring clip(s), or support pin(s) that extend across and/or buttress the underside of the push plate 116. As another option, one or more pairs of opposing flexible tabs 136A, 136B and 136C may be attached to or integrally formed with the sensor clip's 110 skeletal frame proximate the base 122 such that the tabs project transversely into the aperture 134, as seen in FIG. 3D, to provide subjacent support to the sensor stack 114. The tabs 136A, 1368, 136C are fabricated from a compliant material such that, when the test sensor stack 114 is pushed or otherwise passed through the aperture 134 in the bottom 122 of the sensor clip 110, the tabs 136A, 136B, 136C flex (e.g., upwardly in FIGS. 3A and 3B) wider the force of the moving sensors 112 to allow the stack 114 to pass into the internal chamber 128. Once the entire stack 114 is situated inside the chamber 128, the elastic tabs 136A, 136B, 136C flex back to their original orientation such that the push plate 116 is seated on top of and supported by the tabs 136A, 136B, 136C.

One or more or all of the tabs 136A, 136B, 136C could be fabricated with chamfered or rounded edges to facilitate the insertion of the stack 114. As another option, the tabs 136A, 136B, 136C and/or rails 130A, 130B can be provided with structural interfaces for mating with a mechanical mechanism in the manufacturing equipment such that the equipment can pull and hold the tabs apart while the stack 114 is inserted into the clip 110. In this regard, the structural gaps between the rails 130A, 130B can be used by the manufacturing equipment to hold the preformed stack of strips 114 for insertion into clip 110. As another option, the tabs 136A, 136B, 136C could be constructed as separate pieces that are attached to the bottoms of the elongated rails 130A, 130B after the stack 114 is inserted into the clip 110. The tabs 136A, 136B, 136C could be fastened by various means, including snap fit or friction fit.

Turning back to FIG. 3C, the top 120 of the skeletal frame is covered by a cap 138 with an elongated slot 140 extending the length thereof. The slot 140 is configured to receive an ejection mechanism for advancing the test sensors 112 out of the internal chamber 128 of the sensor clip's 110 skeletal frame. A thumb-activated sensor ejection mechanism (FIGS. 4A and 4B), also known as a "picker" or "pusher tab" in the art, may be operatively coupled to the top 120 of the sensor clip 110 and configured to slide horizontally along the length of the cap 138. A projection or "foot" protrudes from the bottom of the picker, through the slot 140, and into the chamber 128 to engage at least the top-most test strip 112 which lies flush against the bottom of the cap 138. The foot can be designed to engage and excise only a single test sensor at a given time or, in some configurations, can engage and excise multiple test sensors. The foot can reciprocally move from a standby position, e.g., towards the far left in FIG. 3A, whereat the foot engages one end of a test sensor, to an ejection position, e.g., towards the far right in FIG. 3A, whereat the foot pushes at least a portion of the test sensor through the sensor slot 118. Some non-limiting examples of sensor ejection mechanisms that may be used with the sensor clip assembly 100 are described in U.S. Pat. Nos. 7,677,409 and 8,097,210, and International (PCT) Patent Application Publication No, WO 2013/180804. It is also envisioned that the clip 110 have provisions to accommodate various other sensor ejection means, such as an ejection wheel or lever.

To assist in protecting the reagents) of the test sensors 112, desirable packaging material and/or desiccant material may be used. The sensor clip assembly 100 can be packaged in a material that prevents or inhibits air and moisture from entering into the interior 128 of the sensor clip 110. One type of removable packaging that may be used to enclose the sensor clip assembly 100 is aluminum foil. It is contemplated that desiccant material, such as silica gel and other molecular sieve beads, may be added in the interior of the packaging to assist in maintaining an appropriate humidity level therein. The sensor clip assembly 100 may be provided with an optional desiccant pocket 144 for storing the desiccant material. The pocket 144 can be attached to one or more of the sides of the skeletal frame. Alternatively, a desiccant can be adhered directly to the clip, molded into the clip, or can even be formed into or as part of the pusher plate.

As another optional feature, the sensor clip assembly 100 can be provided with an auto-calibration tab 146 that is attached to one or more sides of the sensor clip's 110 skeletal frame. The auto-calibration tab 146 provides detailed calibration information for the sensor clip assembly 100. This information may be read by a glucose meter to determine the brand, type, and/or specifications of the test strips in the clip. Optionally, the meter may make electrical contact with the auto-calibration tab 146 and read the coded calibration information specific to the sensor clip assembly 100. Due to variations in biosensor manufacturing, this coding can allow the glucose meter to be automatically calibrated based on the test strips being used. In addition to detailed calibration information, the auto-calibration tab 146 may contain anti-counterfeiting information, geographic information, date of manufacture information, etc. Additional information regarding auto-calibration information and related technologies can be found in U.S. Pat. Nos. 7,809,512, 8,124,014, and 8,206,564, each of which is incorporated herein by reference.

FIGS. 4A and 4B illustrate an example of a hand-held glucose testing meter 150 for use with the sensor clip assembly 100 shown in FIGS. 3A-D. The meter 150 includes an outer housing 152 with a display 154, a test sensor port 156, and one or more input devices, which may be in the nature of a touchscreen 155 and/or a plurality of pushbuttons 158. For at least some embodiments, the input devices allow a user to toggle between modes, adjust for various test strips, change the settings of the display, such as contrast and/or color, power the device on or off, check to see whether the device is functioning properly, check the battery level, access stored information, and/or enter personal information.

Shown schematically at 160 in HG. 4A are one or more processors and one or more memory devices (which may be representative of "testing electronics") that are located inside the meter 150 and operatively coupled to the display 154, the input devices 155, 158, and test sensor port 156. The testing electronics 160 operatively connect with (e.g., electrically couple to) the test strips 112 to determine analyte concentration information from a fluid sample. The processor may comprise any combination of hardware, software, and/or firmware disposed in and/or disposed outside of the meter housing 152. The memory is operatively coupled to the processor (or may be part of the processor), and is configured to store, among other things, the analyte concentration information. The memory may comprise, for example, volatile memory (e.g., a random-access memory (RAM)), non-volatile memory (e, g, are EEPROM), and combinations thereof. The meter 150 may include other known electronics, such as a communication interface for transmitting and receiving data either via wired or wireless links.

Blood glucose meter 150 includes an internal cartridge chamber 162 with an opening 164 through which the sensor clip assembly 100 is inserted into the outer housing 152 of the meter 150. A flip-top lid 166 is movably attached to the outer housing 152 to cover the internal cartridge chamber opening 164 (and, thus, the sensor clip assembly 110) when the lid 166 is in a closed position. When pressed closed, the flip-top lid 166 can mate with a complementary gasket or other seal mechanism to make an "on meter seal" that provides a vapor-resistant barrier to prolong the use life of the clip of sensors 112. It is desirable, for at least some embodiments, that the internal cartridge chamber 162 be vapor tight to protect the test strips 112. FIG. 4A shows the meter 150 without a sensor clip assembly 100 loaded into the internal cartridge chamber 162, while FIG. 4B shows a sensor clip assembly 100 removably disposed inside the chamber 162 of the meter 150. A pair of spaced alignment tracks 170A and 170B within the outer housing 152 mate with and guide the sensor clip assembly 100 when loaded into the meter housing 152, and also help to keep the assembly 100 properly aligned for repeated use.

A biasing member, such as a pusher spring 168, which extends through the aperture 134 in the bottom 122 of the sensor clip 110, presses against the push plate 116 and drives the sensor stack 114 towards the top of the meter housing 152 (e.g., upwardly in FIG. 48). In so doing, at least one test strip 112 lies flush against the underside surface of the cap 138 for excision through the sensor slot 118 and test sensor port 156 via operation of a thumb-activated sensor ejection mechanism 174. Alternative mechanisms may be used to urge the push plate 116 and test strips 112 to the top of meter 150. For example, a pawl-and-ratchet mechanism may be incorporated into the sensor clip 110 and/or meter housing 152 to provide upward movement of sensors 112. Another non-limiting example of a dispensing system that can be incorporated into the meter 150 is disclosed in U.S. Patent Application Pub. No. 2013/0324822 A1, which was filed on Dec. 28, 2012. In the illustrated example, the ejection mechanism 174 is shown to be part of the meter 150; nevertheless, the sensor clip 110 may be manufactured with a built-in pusher tab or other ejection mechanism. An optional latch mechanism 172, which is disposed on the top of the meter housing 152 adjacent the opening 164, is configured to hold the sensor clip assembly 110 in place when it is inserted into the meter 150. The latch mechanism 172 may take on various known forms, such as a spring-loaded clip.

Figure 5A:
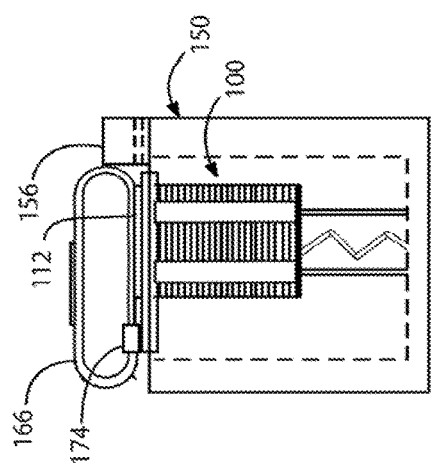
FIGS. 5A-5D are diagrammatic illustrations showing a representative method for using of the sensor clip assembly of FIGS. 3A-D with the analyte testing meter of FIGS. 4A and 4B in accordance with aspects of the present disclosure.
Figure 5B:
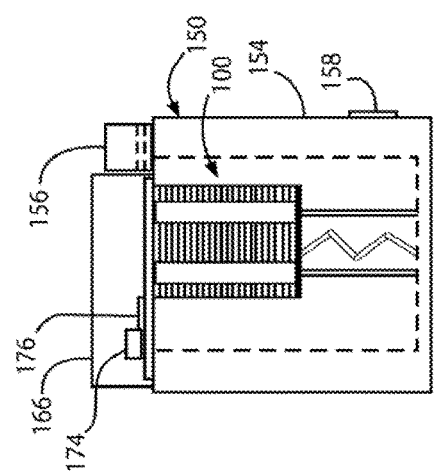
Figure 5C:
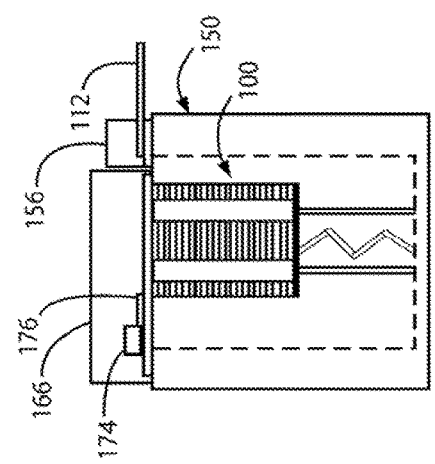
Figure 5D:
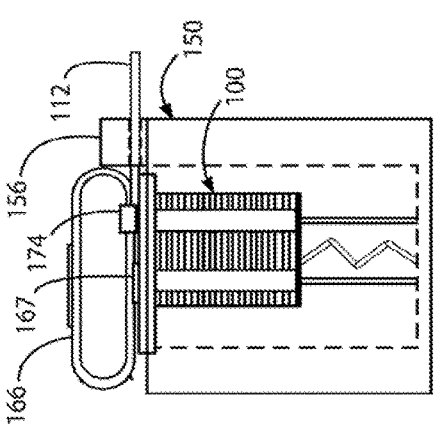

FIGS. 5A-D illustrate the sensor dip assembly 100 disposed within the blood glucose meter 150. FIG. 5A shows the clip 110 loaded into the meter 150 with the flip-top lid 166 closed and the thumb-activated "pusher" ejection mechanism 174 in the standby position such that a test strip 112 has not been deployed from the sensor clip assembly 100 into the test sensor port 156. In use, the user may open the blood glucose meter 150 by flipping the lid 166 over a hinge 167 (FIG. 5C) at the top of the meter 150 to reveal the ejection mechanism 174, as seen in FIG. 5B. The user may then slide the ejection mechanism 174 across the top of the meter 150 (to the right in the illustrations of FIGS. 5A-5D) from the standby position (FIG. 5B) to the election position (FIG. 5C) to thereby excise a test strip 112 from the sensor clip assembly 100. When the ejection mechanism 174 reaches the ejection position, the test strip 112 is passed into and at least partially out of the test sensor port 156, as best seen in FIG. 5C. At this point, a blood sample (or other test sample) may be placed on the protruding test strip 112 to obtain a measurement of blood glucose (or other analyte) in the sample, which may be presented to the user on display 154. In some optional configurations, the meter 150 is activated and the user is automatically prompted to take a measurement when the lid 166 is shut with a test strip 112 in the test sensor port 156, as seen in FIG. 5D.

Coupled with an optional contact switch 176 that detects the position of the lid 166, the meter 150 may be provided with one or more thermal sensors (not shown) to sense temperature changes while the lid 166 is open to detect a mismatch between the ambient temperature and the meter's 150 internal temperature which can affect performance. If a mismatch is detected, the internal testing electronics 160 of the meter 150 can be configured to automatically trigger an algorithmic correction or, in extreme cases, not allow a test to be performed. In a similar regard, the meter 150 could be outfitted with sensors to monitor ambient and internal humidity to make sure that the reagent is properly protected. The contact switch 176 can also be used to generate a reminder to the user to close the lid 166.

Figure 6:
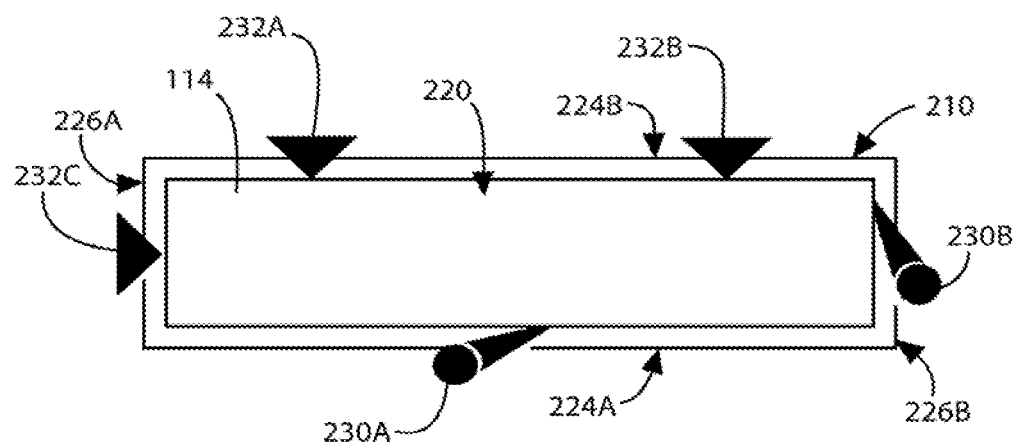
FIG. 6 is a schematic top-view illustration of another representative sensor clip for a stacked sensor dispensing system in accordance with aspects of the present disclosure.

FIG. 6 is a schematic top-view illustration of another representative sensor clip 210 for a stacked sensor dispensing system. The sensor clip 210 can be similar in design, function and operation to the sensor clip 110 discussed above with respect to FIGS. 3A-3D and, thus, can include any of the options, features and alternatives described above. For instance, the sensor clip 210 includes a skeletal frame with a top 220, a bottom (not visible in the view provided), first and second lateral sides 224A and 224B, respectively, and first and second longitudinal sides 226A and 226B, respectively. A test sensor stack 114 is stowed within an internal chamber defined between the sides 224A, 224B, 226A, 226B of the sensor clip 210. The second lateral side 224B of the skeletal frame comprises or consists essentially of two adjacent, substantially parallel, elongated rails 232A and 232B, which may be identical in nature to the rails 132A, 132B in FIG. 3B. Likewise, the first longitudinal side 226A comprises an elongated rail 232C with structural gaps on opposing sides thereof.

In the embodiment illustrated in FIG. 6, the first lateral side 224A and the second longitudinal side 226B of the sensor clip's 210 skeletal frame each comprises one or more compliant alignment rails 230A and 230B, respectively, which are configured to align the test sensor stack 114 within the clip 210. For instance, the position of the sensor stack 114 is controlled by the fixed guide rails 232A-C, while the compliant projections on the alignment rails 230A and 230B cooperatively urge the stack 114 toward a desired "home" position when the clip 210 is loaded with the stack 114 (e.g., during manufacturing fill). In addition, the fixed guide rails 232A-C on the clip 210 can interact with the walls of a meter housing (e.g., housing 152 of FIGS. 4A-4B) to strengthen them and hold the stack 114 in alignment inside a meter (e.g., glucose meter 150 of FIGS. 4A-4B.

Figure 7:
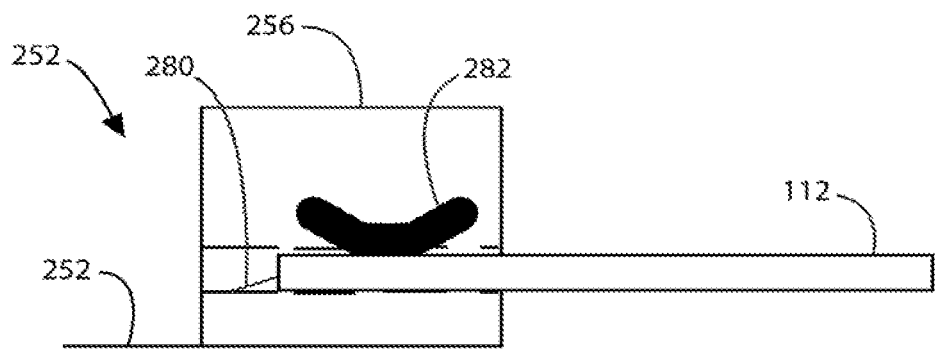
FIG. 7 is schematic side-view illustration of an optional one-way strip port for an analyte testing meter in accordance with aspects of the present disclosure.

FIG. 7 is an enlarged side-view illustration of an optional test sensor port 256 that is attached to the housing 252 of another representative meter 250. The meter 250 can be similar in design, function and operation to the meter 150 discussed above with respect to FIGS. 4A and 4B and, thus, can include any of the options, features and alternatives described above. The test sensor part 256 is provided with a spring-loaded stop 280 that can be pressed downwards to allow the test strip 112 to into and pass through the port 256, but is biased upward to abut an obstruct the rear of the strip 112 and thereby prevent the test strip 112 from being inadvertently pushed backward (e.g. to the left in FIG. 7) into the meter 250 during handling and blood drop acquisition. The test sensor port 256 can also be provided with one or more spring loaded electrical contacts 282 that are biased downwards to apply a compressive force on the test strip 112 to keep the strip 112 from slipping back up over the anti-reverse stop 280.

Figure 8:
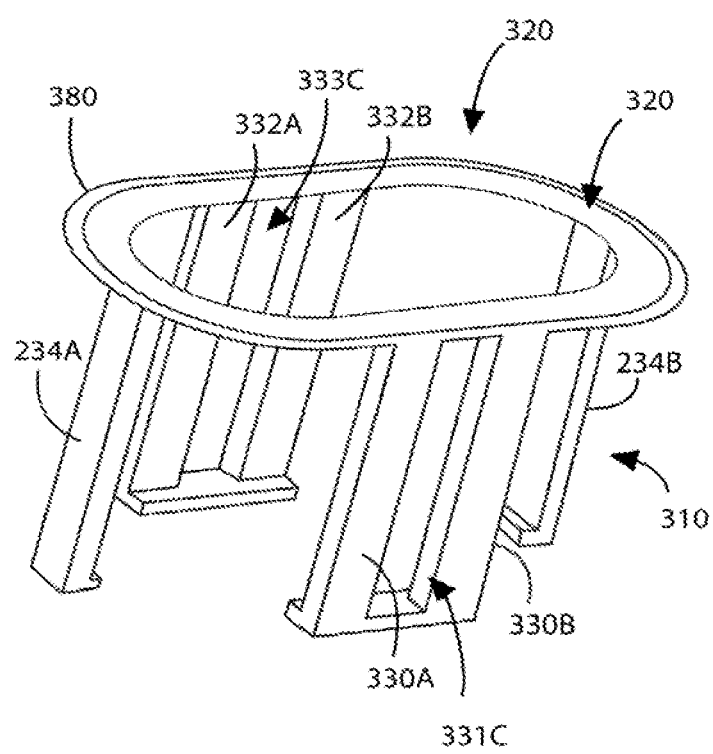
FIG. 8 is a perspective-view illustration of a representative test sensor clip with a flexible seal in accordance with aspects of the present disclosure.

FIG. 8 illustrates a representative test sensor clip 310 for use in a multi-strip analyte testing meter, such as the hand-held glucose meter 150 shown in FIGS. 4A and 4B. Unless otherwise logically prohibited, the architecture shown in FIG. 8 may include any of the features, options and alternatives described above with respect to the architecture shown in FIGS. 3A-3D, and vice versa. For instance, sensor clip 310 can be used to both store and dispense a plurality of biosensors or test strips, such as the test strips 112 described above in connection with FIG. 3A. Also similar to the sensor clip 110 of FIGS. 3A-3D, the sensor clip 310 of FIG. 8 comprises a skeletal frame with one or more "open" faces. By way of example, the first lateral side of the skeletal frame of FIG. 8 comprises or consists essentially of two adjacent, substantially parallel, elongated rails 330A and 330B that are spaced from one another by a centrally located structural gap 331C. Likewise, the second lateral side of the clip's 310 skeletal frame comprises or consists essentially of two adjacent, substantially parallel, elongated rails 332A and 332B that are spaced from one another by a centrally located structural gap 333C. Likewise, the longitudinal sides of the clip 310 may each comprise a respective elongated rail 234A and 234B with structural gaps on opposing sides thereof.

In the embodiment illustrated in FIG. 8, a gasket or O-ring type seal member 380 is attached to or integrally formed with the top 320 of the clip 310. The flexible seal member 380 extends continuously or substantially continuously around the outer edge of the top 320 of the clip 310, e.g., at the base of a cap (e.g., cap 138 of FIGS. 3A-3D), to form a seal between durable surfaces on the clip and a meter or a storage container. For example, the flexible seal member 380 can be configured to compress against or otherwise mate with and thereby form a vapor-tight seal between a lid of a meter (e.g., flip-top lid 166 of FIGS. 4A and 4B) and the top 320 of the clip 310. This seal could be a standalone seal or implemented with a separate durable seal for redundancy.

While many embodiments and modes for carrying out the present invention have been described in detail above, those familiar with the art to which this invention relates will recognize various alternative designs and embodiments for practicing the invention within the scope of the appended claims.

What is claimed is:

1. A removable sensor clip assembly for storing and dispensing analyte testing sensors in a housing, the removable sensor clip assembly comprising:
   a plurality of analyte test sensors arranged in a stack, each of the plurality of analyte test sensors configured to assist in testing an analyte in a fluid sample;
   a skeletal frame with a top, a bottom, and a plurality of sides, the top, the bottom, and the plurality of sides being interconnected to define an internal chamber within which is stored the plurality of analyte test sensors,
   wherein the plurality of sides comprises:
      a first lateral side opposing a second lateral side; and
      a first longitudinal side opposing a second longitudinal side,
      wherein the first lateral side and the second lateral side is each formed as a pair of elongated rails separated by a first structural gap, and
      wherein each of the first longitudinal side and the second longitudinal side is formed as a single elongated rail;
   wherein each of the plurality of sides is spaced from adjacent sides by another structural gap; and
   a flexible seal member extending continuously around an outermost edge of the top of the skeletal frame, the flexible seal member configured to mate with an interior wall of a sensor clip assembly housing thereby forming a vapor-tight seal between the interior wall and the top of the skeletal frame.

2. The removable sensor clip assembly of claim 1, wherein the bottom of the skeletal frame defines an aperture configured to receive therethrough the plurality of analyte test sensors.

3. The removable sensor clip assembly of claim 1, wherein the bottom of the skeletal frame includes a pair of opposing flexible tabs configured to receive therethrough the plurality of analyte test sensors, the pair of opposing flexible tabs being configured to retain the plurality of analyte test sensors inside the internal chamber and flex such that the plurality of analyte test sensors can pass through the bottom of the skeletal frame into the internal chamber.

4. The removable sensor clip assembly of claim 1, further comprising a cap covering the top of the skeletal frame, the cap including an elongated slot configured to receive therethrough an ejection mechanism for advancing the plurality of analyte test sensors, one at a time, out of the internal chamber of the skeletal frame.

5. The removable sensor clip assembly of claim 4, wherein a top-most test sensor from the plurality of analyte test sensors lies flush against a bottom of the cap.

6. The removable sensor clip assembly of claim 1, wherein each of the pair of the elongated rails and each of the single elongated rails are columnar, extending between and connecting the top and the bottom of the skeletal frame.

7. The removable sensor clip assembly of claim 1, wherein at least one of the plurality of sides of the skeletal frame comprises one or more compliant alignment rails configured to align the plurality of analyte test sensors within the internal chamber.

8. The removable sensor clip assembly of claim 1, further comprising a push plate on which is seated the plurality of analyte test sensors.

9. The removable sensor clip assembly of claim 1, further comprising a pocket attached to the skeletal frame, the pocket being configured to store therein a desiccant material.

10. The removable sensor clip assembly of claim 1, further comprising an auto-calibration tab attached to the skeletal frame, the auto-calibration tab including detailed calibration information for the removable sensor clip assembly.

11. The removable sensor clip assembly of claim 1, wherein the plurality of analyte test sensors includes electrochemical sensors, each of the electrochemical sensors includes a base, one or more electrodes supported by the base, and a reagent in electrical communication with the one or more electrodes, the reagent including an enzyme that is adapted to chemically react with the analyte.

12. The removable sensor clip assembly of claim 1, wherein the plurality of analyte test sensors includes optical sensors.

13. An analyte testing system, comprising:
a sensor clip assembly for storing and dispensing a plurality of analyte test sensors arranged in a stack, the plurality of analyte test sensors configured to receive a fluid sample and generate an indication of a characteristic of an analyte in the fluid sample,
wherein the sensor clip assembly includes a skeletal frame with a top, a bottom, and a plurality of sides,
wherein the top, the bottom, and the plurality of sides are interconnected to define a first internal chamber within which is stored the plurality of analyte test sensors,
wherein the plurality of sides comprises:
a first lateral side opposing a second lateral side; and
a first longitudinal side opposing a second longitudinal side,
wherein the first lateral side and the second lateral side are each formed as a pair of elongated rails separated by a first structural gap, and
wherein each of the first longitudinal side and the second longitudinal side are formed as a single elongated rail, and
wherein each of the plurality of sides is spaced from adjacent sides by another structural gap;
a meter with a housing defining a second internal chamber with an opening, the meter including testing electronics configured to analyze the indication of the characteristic of the analyte generated by each of the plurality of analyte test sensors,
wherein the sensor clip assembly is removably disposed inside the second internal chamber of the housing; and
a flexible seal member extending substantially continuously around an outermost edge of the top,
wherein the flexible seal member is configured to compress against an interior perimeter wall of the second internal chamber of the housing thereby forming a vapor tight seal between the interior perimeter wall and the top of the skeletal frame.

14. The analyte testing system of claim 13, wherein the bottom of the skeletal frame includes a pair of opposing flexible tabs configured to receive therethrough the plurality of analyte test sensors, the pair of opposing flexible tabs being configured to retain the plurality of analyte test sensors inside the first internal chamber and flex such that the plurality of analyte test sensors can pass through the bottom of the skeletal frame into the first internal chamber.

15. The analyte testing system of claim 13, further comprising a cap covering the top of the skeletal frame, the cap including an elongated slot configured to receive therethrough an ejection mechanism for advancing the plurality of analyte test sensors, one at a time, out of the first internal chamber of the skeletal frame.

16. The analyte testing system of claim 15, wherein a top-most test sensor from the plurality of analyte test sensors lies flush against a bottom of the cap.

17. The analyte testing system of claim 13, wherein each of the pair of the elongated rails and each of the single elongated rails are columnar, extending between and connecting the top and the bottom of the skeletal frame.

18. The analyte testing system of claim 13, wherein the plurality of analyte test sensors includes electrochemical sensors, each of the electrochemical sensors includes a base, one or more electrodes supported by the base, and a reagent in electrical communication with the one or more electrodes, the reagent including an enzyme that is adapted to chemically react with the analyte.

19. The analyte testing system of claim 13, wherein the plurality of analyte test sensors includes optical sensors.

20. An analyte testing system, comprising:
an analyte testing device comprising:
a housing; and
at least one thermal sensor for detecting a mismatch between an ambient temperature and an internal temperature of the analyte testing device,
wherein the analyte testing system is configured to perform a corrective measure upon detection of the mismatch; and
a sensor clip assembly, comprising:
a skeletal frame for storing a plurality of test sensors, the skeletal frame comprising:
a top comprising an outer edge;
a bottom; and
a plurality of sides extending between the top and the bottom, each of the plurality of sides separated from adjacent sides by a first structural gap,
wherein the top, the bottom, and the plurality of sides are interconnected to define an interior in which the plurality of test sensors is stored,
wherein the plurality of sides comprises:
a first lateral side opposing a second lateral side; and
a first longitudinal side opposing a second longitudinal side,
wherein the first lateral side and the second lateral side is each formed as a pair of elongated rails separated by a second structural gap, and
wherein each of the first longitudinal side and the second longitudinal side is formed as a single elongated rail.

* * * * *